US009743739B2

(12) United States Patent
Parisi et al.

(10) Patent No.: US 9,743,739 B2
(45) Date of Patent: Aug. 29, 2017

(54) HYGIENIC RAZOR BLADE DRYER

(71) Applicant: Toilettree Products, Inc., Upper Nyack, NY (US)

(72) Inventors: Steven Parisi, Haverstraw, NY (US); Gary Parisi, Congers, NY (US); Paul Parisi, San Diego, CA (US)

(73) Assignee: Toilettree Products, Inc., Upper Nyack, NY (US)

( * ) Notice: Subject to any disclaimer, the term of this patent is extended or adjusted under 35 U.S.C. 154(b) by 0 days.

(21) Appl. No.: 14/943,727

(22) Filed: Nov. 17, 2015

(65) Prior Publication Data

US 2016/0066675 A1    Mar. 10, 2016

Related U.S. Application Data

(63) Continuation-in-part of application No. 13/911,754, filed on Jun. 6, 2013, now Pat. No. 9,186,802, which is a continuation of application No. 12/917,533, filed on Nov. 2, 2010, now Pat. No. 8,458,922.

(60) Provisional application No. 61/257,265, filed on Nov. 2, 2009.

(51) Int. Cl.
| | |
|---|---|
| *F26B 13/30* | (2006.01) |
| *A45D 27/48* | (2006.01) |
| *A61L 2/10* | (2006.01) |
| *F26B 3/28* | (2006.01) |
| *F26B 9/00* | (2006.01) |
| *A45D 27/46* | (2006.01) |

(52) U.S. Cl.
CPC ............. *A45D 27/48* (2013.01); *A45D 27/46* (2013.01); *A61L 2/10* (2013.01); *F26B 3/28* (2013.01); *F26B 9/003* (2013.01); *A61L 2202/24* (2013.01)

(58) Field of Classification Search
CPC .......... F26B 13/00; F26B 13/30; B26B 19/38; B26B 19/3806; A45D 27/00; A45D 27/48
USPC ............. 34/412, 90; 250/453.1; 422/292, 28
See application file for complete search history.

(56) References Cited

U.S. PATENT DOCUMENTS

| | | | |
|---|---|---|---|
| 1,595,440 A | | 4/1925 | Winslow |
| 1,550,334 A | * | 8/1925 | Baxter ................... A45D 27/48 |
| | | | 219/521 |
| 1,956,743 A | * | 5/1934 | Lifton .................... A45D 27/48 |
| | | | 15/218 |

(Continued)

FOREIGN PATENT DOCUMENTS

| | | |
|---|---|---|
| GB | 2117304 | 10/1983 |
| JP | 2002-166072 | 6/2002 |

(Continued)

OTHER PUBLICATIONS

International Search Report and Written Opinion issued by KIPO mailed on Jun. 23, 2011, for corresponding International Application No. PCT/US2010/055031.

*Primary Examiner* — Stephen M Gravini
(74) *Attorney, Agent, or Firm* — Myers Wolin, LLC (57) ABSTRACT

A hygienic razor blade dryer is provided that comprises a housing having an interior, a razor blade holder disposed within the interior that is adapted to receive a razor blade, a dryer for drying a razor blade received in the razor blade holder, and a vacuum for evacuating the air within the interior to prevent moisture buildup in the air and on the razor blade and to inhibit oxidation on the blade surfaces. A sanitizer may also be provided to sanitize the razor blade before, during or after the dryer operation.

13 Claims, 12 Drawing Sheets

(56) References Cited

U.S. PATENT DOCUMENTS

| | | | | |
|---|---|---|---|---|
| 2,748,413 | A * | 6/1956 | Morrow | A45D 27/48 15/218 |
| 3,172,416 | A | 3/1965 | Simmons | |
| 3,759,594 | A | 9/1973 | Cobb | |
| 4,480,394 | A | 11/1984 | Salas | |
| 5,241,751 | A | 9/1993 | Goh | |
| 5,487,877 | A | 1/1996 | Choi | |
| 6,102,055 | A | 8/2000 | Karnatz | |
| 6,874,247 | B1 | 4/2005 | Hsu | |
| 6,946,624 | B1 | 9/2005 | Tomassetti | |
| 7,134,935 | B1 | 11/2006 | Papetti | |
| 7,225,559 | B1 | 6/2007 | Padilla | |
| 7,263,738 | B2 | 9/2007 | Moore | |
| 7,743,506 | B2 | 6/2010 | Szczepanowski et al. | |
| D622,160 | S | 8/2010 | Bridges | |
| 7,858,027 | B2 | 12/2010 | Trissel | |
| 8,296,493 | B1 | 10/2012 | Engelhardt et al. | |
| 8,458,922 | B2 * | 6/2013 | Parisi | A45D 27/48 108/115 |
| 9,186,802 | B2 * | 11/2015 | Parisi | A45D 27/48 |
| 2003/0034459 | A1 | 2/2003 | Bonin | |
| 2005/0101231 | A1 | 5/2005 | Sekerich | |
| 2005/0252793 | A1 | 11/2005 | Wilkinson | |
| 2006/0042103 | A1 | 3/2006 | Chasen | |
| 2008/0060671 | A1 | 3/2008 | Ruffin | |
| 2008/0060689 | A1 | 3/2008 | Takizawa et al. | |
| 2008/0128407 | A1 | 6/2008 | Cohn | |
| 2008/0168677 | A1 | 7/2008 | Miller | |
| 2008/0178489 | A1 | 7/2008 | Dionne | |
| 2008/0178897 | A1 | 7/2008 | Gallagher | |
| 2008/0282576 | A1 | 11/2008 | Ueda et al. | |
| 2009/0019702 | A1 | 1/2009 | Wevers et al. | |
| 2009/0183379 | A1 | 7/2009 | Johnson | |
| 2009/0183384 | A1 * | 7/2009 | Kitamura | A45D 27/48 34/247 |
| 2011/0099831 | A1 | 5/2011 | Parisi et al. | |
| 2015/0059197 | A1 * | 3/2015 | Sassano | A45D 27/48 34/80 |
| 2016/0066675 | A1 * | 3/2016 | Parisi | A61L 2/10 34/443 |

FOREIGN PATENT DOCUMENTS

| | | | |
|---|---|---|---|
| JP | 2006-075188 | 3/2006 | |
| JP | 2008-061880 | 3/2008 | |
| WO | 9806546 | 2/1998 | |
| WO | WO 2011053947 A2 * | 5/2011 | ............ A45D 27/48 |
| WO | WO 2011053947 A3 * | 8/2011 | ............ A45D 27/48 |

* cited by examiner

HYGIENIC RAZOR BLADE DRYER

CROSS-REFERENCE TO RELATED APPLICATIONS

This application is a continuation in part of U.S. patent application Ser. No. 13/911,754, filed Jun. 6, 2013, which is a continuation of U.S. patent application Ser. No. 12/917,533, filed Nov. 2, 2010, now U.S. Pat. No. 8,458,922, which claims the benefit of U.S. Patent Application 61/257,265 filed Nov. 2, 2009, the contents of each of which are incorporated herein by reference in their entirety.

FIELD OF THE INVENTION

The present invention relates to dryers generally, and more particularly, in one embodiment, to a razor blade dryer having a chamber for holding a razor blade and a dryer for removing moisture from the blade.

BACKGROUND

Wet shaving razors come in several types including the disposable type (with single or multiple blades) or of the type using disposable blades. All such shaving razor's blades generally become dull and undesirable for use (or unusable) after several uses. The dullness of the blade is caused by several mechanisms. One mechanism is the actual abrasive effect of the blade cutting through hairs and rubbing against skin. Repeated use of a razor over time inevitably produces this dulling effect.

A second mechanism that results in effective dulling (or equivalent degradation of effectiveness) of the razor blade is corrosion of the blade surface and cutting edge caused by oxidation that occurs when a wet blade is left to air dry. This occurs primarily after shaving when the wet blade is stored away until the next use. However, depending on the storage location of the blade, such as on a bathroom counter or in a shower, which are both high humidity environments, the blade can be exposed to additional sources of ambient moisture that results in the re-wetting of the blade followed by a subsequent drying. Thus, a razor blade may experience many wet-dry cycles during the day, which can accelerate the degradation of the blade over time.

While the closeness and effectiveness of a shave appears to a user to degrade with repeated use of a razor blade over time, it has been determined that the second mechanism relating to oxidation results in the most actual damage to the blade. Dryers for razor blades are known in the art and generally focus on the drying of a blade immediately after use. However, such prior art dryers fail to address environmental moisture buildup that promotes oxidation during periods when the razor blade is being stored or is otherwise exposed to moisture that is unrelated to the act of shaving.

SUMMARY

A hygienic razor blade dryer is provided that comprises a housing having an interior, a razor blade holder disposed within a carriage that is adapted to receive a razor, and a dryer for drying a razor blade received in the razor blade holder. A vacuum or a sanitizer light and/or spray may also be provided to sanitize and disinfect the razor blade before, during or after the dryer operation.

DETAILED DESCRIPTION OF THE PREFERRED EMBODIMENTS

This disclosure describes the best mode or modes of practicing the invention as presently contemplated. This description is not intended to be understood in a limiting sense, but provides an example of the invention presented solely for illustrative purposes by reference to the accompanying drawings to advise one of ordinary skill in the art of the advantages and construction of the invention. In the various views of the drawings, like reference characters designate like or similar parts.

Figures 1, 2:
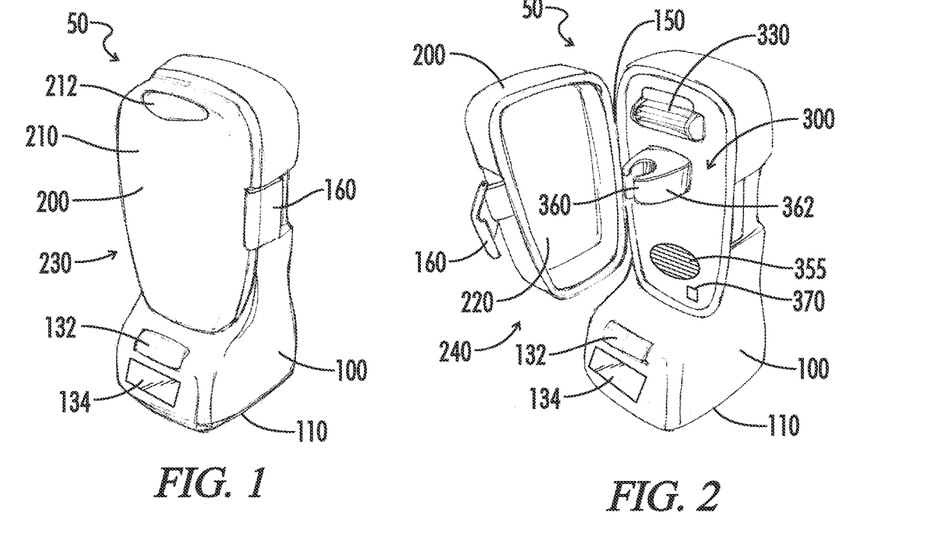
FIG. 1 is a perspective view of one embodiment of a hygienic razor blade dryer device of the present invention in the closed position.
FIG. 2 shows the device of FIG. 1 in the open position.
Figure 3:
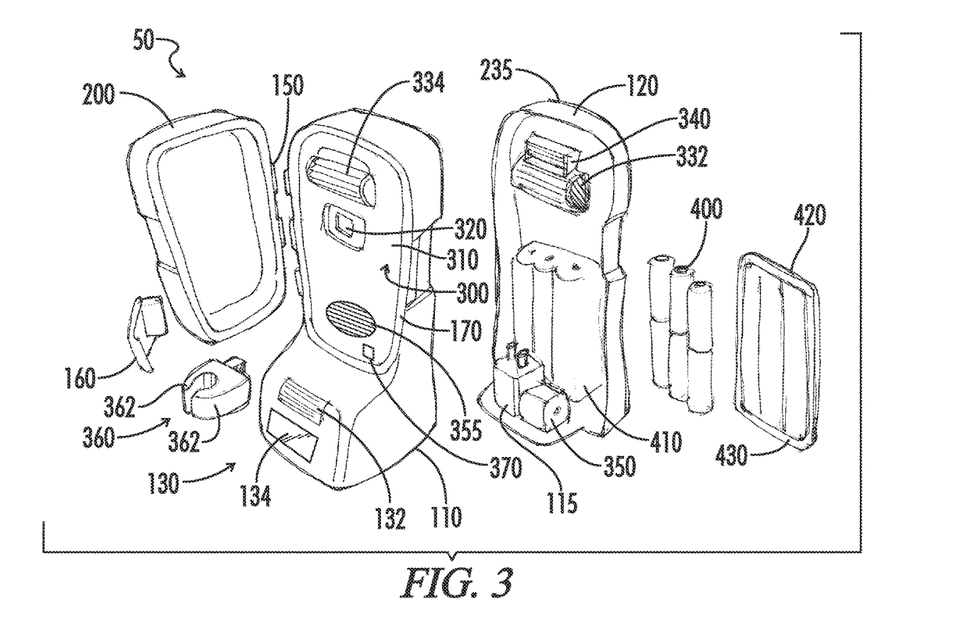
FIG. 3 is an exploded view of the device of FIG. 1.
Figure 4:
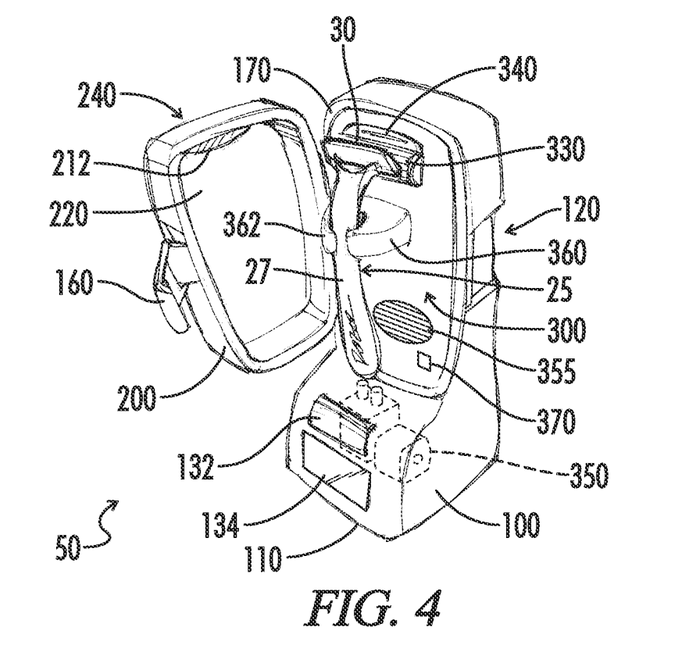
FIG. 4 shows one embodiment of a hygienic razor blade dryer device of the present invention in the open position with the razor secured therein.

FIG. 1 is a perspective view of one embodiment of a dryer device 50 of the present invention in a closed position, with FIG. 2 illustrating the device 50 in the open position and FIG. 3 illustrating an exploded view of one embodiment of the assembly of the device 50. FIG. 4 shows one embodiment the device 50 in use. While the drying device 50 of FIGS. 1-4 is shown and described for use with a single shaving razor blade 25 (FIG. 4), it is not intended to be limited for use with such an implement. For example, the dryer device could be used with other personal care devices such as a toothbrush, flosser, dental pick and the like, and beauty care devices such as tweezers, nail clippers and the like, where the holder for the implement would be dimensioned and configured accordingly. For purposes of explanation, the device 50 will be shown and described for use with a single shaving razor blade, it being understood that other uses are contemplated.

One embodiment of the device 50 further comprises a housing 100 having a base 110 and a back 120, a door 200 having an exterior 210 and an interior 220 and that is movable relative to the housing 100 via a hinge 150 between a closed position 230 as shown in FIG. 1 and an open position 240 as shown in FIGS. 2-4, and a latch 160 for securing the door 200 to the housing 100. In this particular embodiment, the base 110 is shaped to support the housing 100 in an upright position, although it will be understood that the housing 100 could also positioned in different orientations such as, for example, in a horizontal orientation with the back 120 of the housing 100 resting on a support surface (not shown). The device 50 could also include components for securing the device 50 to a counter or wall, for example, such as suction cups (not shown) on the base 110 and/or back 120 or other mounting components as desired. The back 120 could also contain a retractable component to assist the device 50 in standing upright, similar to a leg on a picture frame.

The device 50 further comprises an interior 300 that is defined between the housing 100 and the door 200. The interior 300 is exposed when the door 200 is in the open position 240, and is sealed from the ambient surroundings when the door 200 is in the closed position 230. In the present embodiment, an air-tight seal for the interior 300 is created through the use an O-ring seal 170 defined between the housing 100 and the door 200, the seal 170 being embedded in or otherwise retained by either the housing 100 or the door 200. While an O-ring seal 170 is shown and described, it will be appreciated that other methods of sealing are contemplated. The interior 300 may be viewed through a translucent or transparent window 212 in the door 200 in order to determine if the interior 300 is occupied by an implement or in use. The interior 300 may also be provided with a light (not shown) to better illustrate if the interior 300 is occupied by an implement through the window 212.

The device 50 may be formed from a variety of materials and may be manufactured by a variety of methods. Since the device 50 is likely to be used in a humid environment such as a bathroom for example, it is preferred if the device is not made from material that will react negatively with or degrade upon exposure to moisture and the like. Furthermore, the housing 100 is preferably provided with water-resistant components and air- and water-tight seals to further protect the components from water damage. In one embodiment, the door 200 could be provided with a reflective material, such as a fogless mirror (not shown) for example, on the exterior 210 or the interior 220 that could be utilized during shaving if desired.

Figure 6:
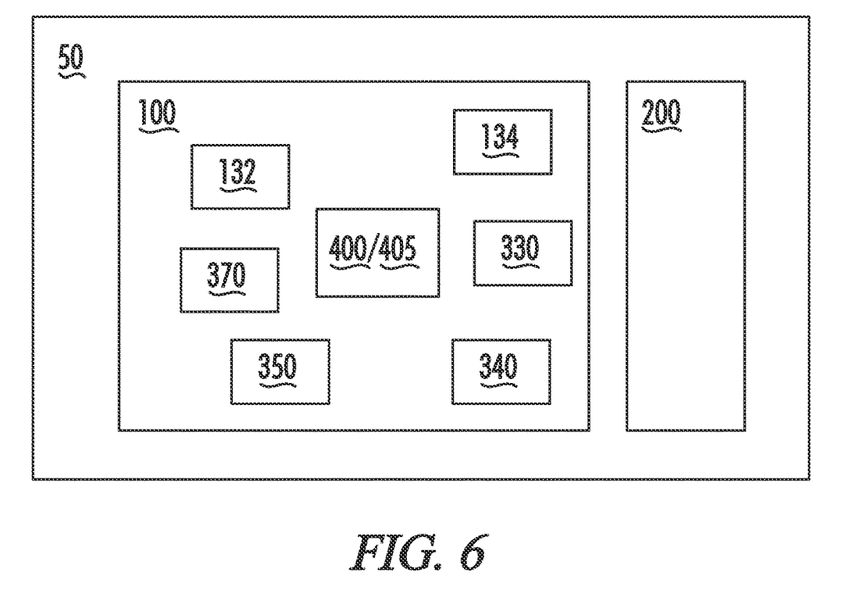
FIG. 6 is a system schematic of one embodiment of a hygienic razor blade dryer device of the present invention.

As shown in FIG. 3, the interior 300 further comprises a wall 310, a razor holder mount 320 provided in the wall 310, a dryer 330 including a fan 332 and directional blades 334, a sanitizer 340 such as an ultraviolet (UV) light, and a vent 355 for the removal of air from the interior. The dryer 330 could be provided with a heating element (not shown) if desired. A vacuum pump 350 disposed in the housing 100 is in fluid communication with the vent 355 in the interior 300 for purposes of evacuating the air from within the interior 300 when so desired and as described below. The powered components of the device 50 are controlled by a CPU 405 (FIG. 6) and energized by a power source 400 shown in the embodiment of FIG. 3 as a plurality of "AA" batteries that are retained in a chamber 410 in the housing 100 by a door 420 having an O-ring seal 430. While "AA" batteries are shown as the power source 400 in the embodiment of FIG. 3, it will be appreciated that other methods of powering the device 50 are contemplated including, but not limited to, other size alkaline batteries, rechargeable batteries, AC, DC, household current, solar and others now known or hereinafter contemplated. If household current is to be used, then the device 50 would be provided with an AC plug and adapter (not shown) or a power cord (not shown) or the like.

The razor holder mount 320 is adapted to receive a razor blade holder 360 having gripping arms 362 that are dimensioned to receive the handle 27 of a razor 25 (FIG. 4). The gripping arms 362 are flexible and resilient to allow for easy insertion and removal of a razor 25 therefrom, and such arms 362 are spaced to accommodate most commonly dimensioned razor handles 27. In one embodiment, the razor blade holder 360 is fixedly attached to the razor holder mount 320. In an alternative embodiment, the razor blade holder 360 is removably attached to the razor holder mount 320 to allow for easy replacement or to allow for the attachment of interchangeable razor blade holders (not shown) of various dimensions for holding razors (not shown) of varying dimensions. In one embodiment, the device 50 could be provided with a variety of interchangeable holders (not shown) and the user would be required to select the holder that most comfortably fits whatever implement will be placed therein. For example, an alternate holder may be provided with two sets of gripping arms (not shown) for holding two razors at a time, or for holding a razor and a toothbrush at the same time. In another alternate example, the gripping arms may be spaced to accommodate a wide handle implement such as, for example, the women's Schick Intuition™ razor.

The razor blade holder 360 resides below the dryer 330 and the sanitizer 340 so that the blade 30 from a razor 25 (FIG. 4) will be adjacent the dryer 330 and sanitizer 340 if the razor 25 is positioned upright in the holder 360. In one embodiment, a deflector hood or shield (not shown) could be positioned above the dryer and sanitizer and surround the razor blade so as to focus and accelerate the drying and sanitizing function on the razor blade. Of course, if the holder 360 is arranged to hold a razor 25 in a downwardly facing position (not shown) where the blade 30 is lower than the handle 27 when retained in the holder 360, then it would be preferred if the dryer 330 and sanitizer 340 were positioned below (not shown) the holder 360 and the vent 355 were positioned above the holder 360. If desired, a deflector hood or shield as discussed above could be utilized in the reverse position as well. While the vent 355 is shown in a certain location, it will be appreciated that it may be positioned anywhere within the interior 300 as long as it functions to remove air from within the interior 300 when desired. In one embodiment, the interior could be provided with multiple dryers and sanitizers (not shown) to account for the various positioning of the razor relative to the razor holder. In another embodiment, the dryer and sanitizer could reside on the door interior 220. Other arrangements are contemplated.

The front 130 of the housing 100 preferably comprises a switch 132 for activating the device 50 as will be described below and a display 134, such as a liquid crystal (LCD) display, for displaying a variety of operational parameters and functions including, but not limited to, a clock, a timer, a night light, temperature, a power meter, operation of the dryer 330, sanitizer 340 and/or vacuum 350, and the relative humidity of the interior 300 obtained from a sensor 370. Other operational features are contemplated. As shown in FIG. 3, the back 120 of the housing 100 is preferably designed to connect via an electrical connector 115 to the interior (not shown) of the front 130 of the housing 100 with an o-ring seal (not shown) acting as an insulator to seal the front and back housing portions 130, 120 respectively. This modular design allows for repair and easy access to the dryer fan 332, sanitizer 340, vacuum pump 350, and power source 400, or other components necessary for the operation of device 50. The exterior housing back 235 could also contain a retractable component to assist the device in standing upright, similar to a leg on a picture frame.

One non-limiting embodiment of an operation of the device 50 will now be described. As shown in FIG. 4, a razor 25 is received within the gripping arms 362 of the razor holder 360 so that the blade 30 of the razor 25 faces the dryer 330 and the sanitizer 340. The door 200 is pivoted from the open position 240 to the closed position 230 (see FIG. 1) and the latch 160 is engaged to create an air-tight chamber in the interior 300 through the use of seal 170. Thereafter, a user (not shown) activates the switch 132 (such as a commercially available pressure or weight sensitive switch) that activates a drying operation. In an alternative embodiment, the drying operation could be initiated simply by closing the door 200 and securing the door latch 160, although such embodiment may incorporate a sensor (not shown) into the razor holder 360 to ensure that the drying operation does not commence unless an implement is being retained by the holder 360. In yet another alternate embodiment, the engagement of the razor 25 with the razor holder 360 could initiate the drying operation, whereby the vacuum 350 would not be activated unless the door 200 is closed and the interior 300 is sealed. Other activation methods are contemplated.

The drying operation can be carried out in a number of ways. In a preferred embodiment, activation of the switch 132 energizes the dryer 330 in accordance with a timer that that is controlled by a central processing unit (CPU) 405 (FIG. 6) control system such as a processor or printed circuit board (PCB) provided in the housing 100. In a preferred embodiment, the drying of the blade 30 is accomplished by a flow of air created by the fan 332 for a certain period of time such as, but not limited to, approximately three minutes, which flow of air is drawn across the blade 30 and evacuated through the vent 355 into the environment outside of the device 50. If desired, a deflector hood or shield (not shown) could surround the blade 30 to focus the air flow as discussed above. Based on a number of environmental factors, such as the relative humidity and temperature of the surroundings, the fan operation may range, for example, from about two minutes to about ten minutes. Other drying times are contemplated. In other embodiments, a heater element (not shown) such as a resistive heating element is incorporated into the fan airstream to heat and dehumidify the blown air or otherwise accelerate the drying operation and reduce the drying time. However, since shaving razors are generally used by only a single individual, and generally no more often than about once per day, the speed of the drying operation may be less important than other factors to consider in any given design. In an alternative embodiment, the drying operation is controlled by a humidity sensor 370 that evaluates the relative humidity in the interior 300 and terminates the drying operation once a certain humidity level is reached. The humidity level may be indicated on the display 134.

Figure 5:
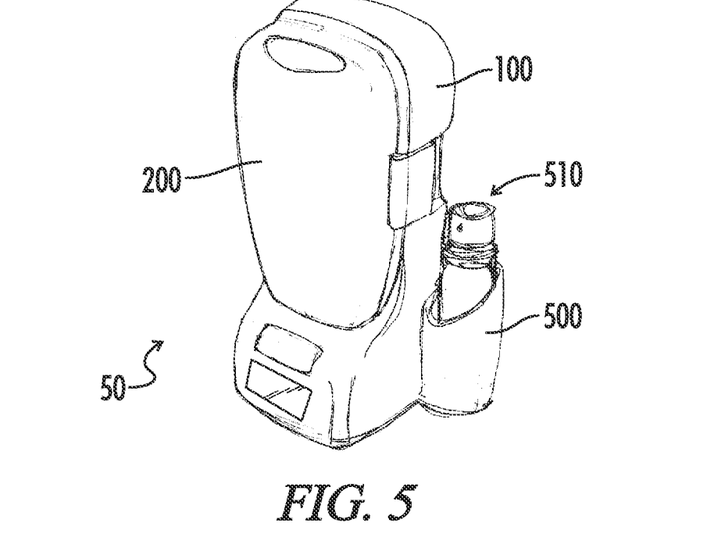
FIG. 5 is a perspective view of another embodiment of a hygienic razor blade dryer device of the present invention including a separate holder for a cleaner or sanitizer.

In a preferred embodiment, the sanitizer 340, such as an ultraviolet (UV) light, is activated during the drying operation. In an alternative embodiment, the sanitizer is activated after the drying operation is complete. Other sanitizing devices such as those that initially spray the razor with a mist of alcohol or other antiseptic, or that generate ozone may also be implemented. Such sanitizing devices may be applied manually by the user or automatically as part of the operation of the device 50 during the drying and sanitizing operation for example. FIG. 5 illustrates an alternative embodiment of a dryer device 50 having a housing 100, a door 200 and a separate holder 500 attached to the housing 100 for storing a cleaner and/or sanitizer 510 or the like that can be applied manually by a user if desired. The separate holder 400 can be integrally attached to the housing 100 during manufacturing of the device 50, of it can be removably attached if it is so desired. While a spray cleaner and/or sanitizer 510 is shown, it will be appreciated that other types of cleaners and/or sanitizers may be used, or other types of peripherals (not shown) such as air fresheners and the like may be stored in the holder 500. The purpose of any cleaning solution is to remove any oils or salts that remain on the blades after being used and to lubricate the blades, while the sanitizer is used to kill any bacteria remaining on the blades.

Returning to the embodiment of FIGS. 1-4, the drying operation is preferably controlled by a timer or a humidity sensor or both. Depending upon the amount of air flow and heat generated, if any, the time for the drying operation can be determined experimentally to provide a suitable level of drying of the razor blade. During or after the drying operation, the vacuum pump 350 evacuates air and moisture through the vent 355 and out of the interior 300 and seals the interior 300 in order to maintain a dry and suitable environment for the stored razor 25 and to prevent oxidation at the blades 30 until it is desired to use the razor 25 again. If a humidity sensor 370 is employed, the drying operation may automatically repeat without user intervention if the relative humidity within the vacuum-sealed interior 300 reaches a certain level. A valve (not shown) is provided to maintain a vacuum seal within the interior 300 once a sufficient amount of air has been evacuated. In one embodiment, pressing of the switch 132 with a vacuum in the interior 300 acts to release the vacuum and enable the user to open the door 200. In another embodiment, a separate button (not shown) could be used to release the vacuum seal, or it can occur simply by disengaging the latch 160.

During operation of the device 50, various parameters may be indicated on the display 134, such as the time of day, the ambient temperature, whether an implement is being retained by the holder 360, the time duration of the drying operation, the amount of time left in the drying operation, whether the sanitizer 340 is activated, whether the vacuum 350 is activated, the relative humidity within the interior 300, whether the interior 300 is vacuum sealed, and whether the device 50 is either turned off or not active. The display 134 may also show whether the device 50 is connected to an external power source such as home current, or whether the device 50 is running on battery power 400 and the amount of battery life remaining. Other operational parameters are contemplated.

Figure 7:
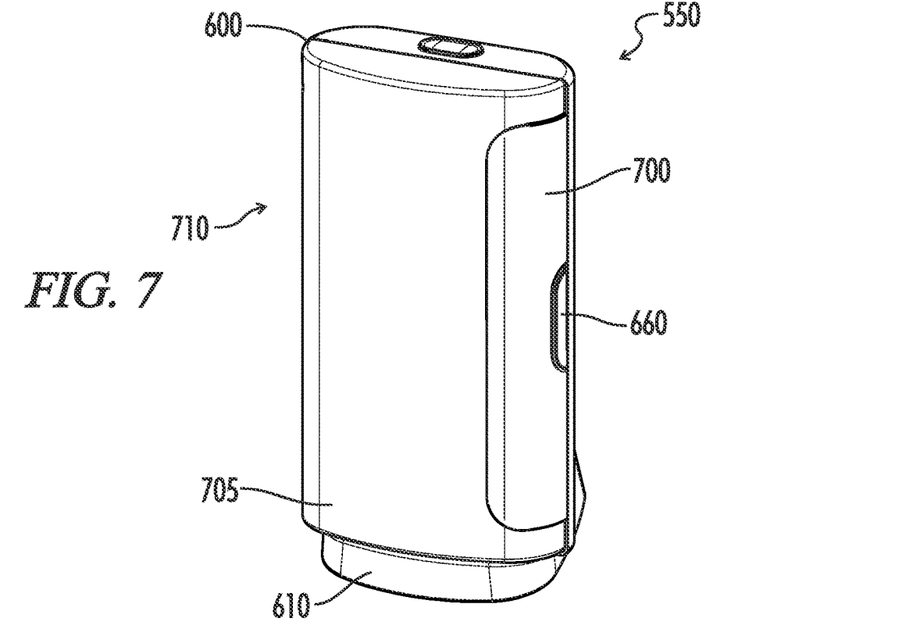
FIG. 7 is a perspective view of an alternative embodiment of a hygienic razor blade dryer device of the present invention in the closed position.
Figure 8:
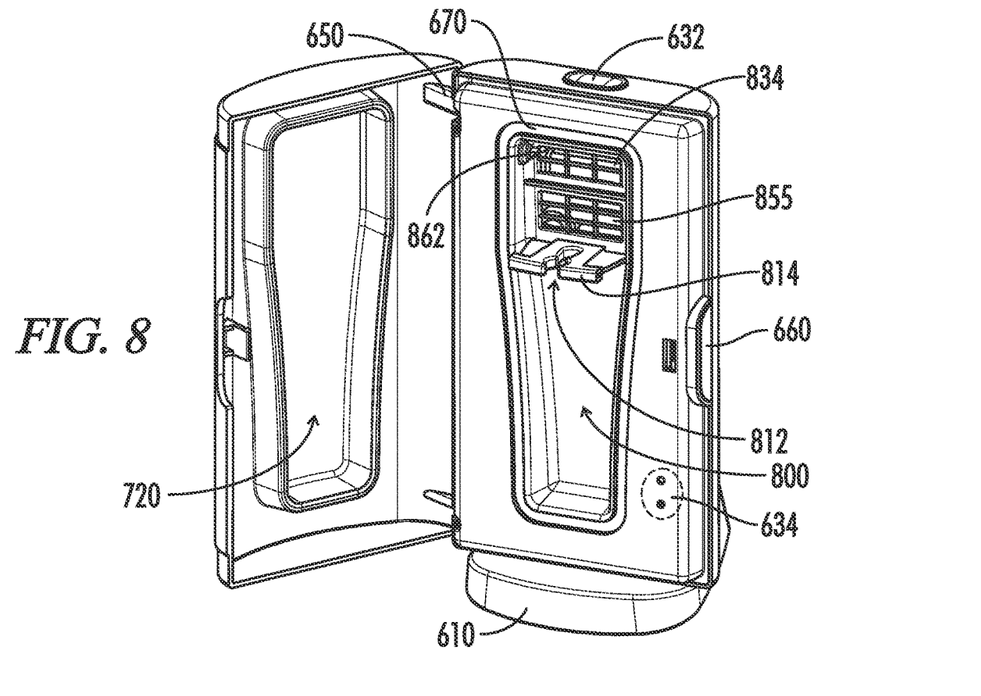
FIG. 8 shows the device of FIG. 7 in the open position.
Figure 9:
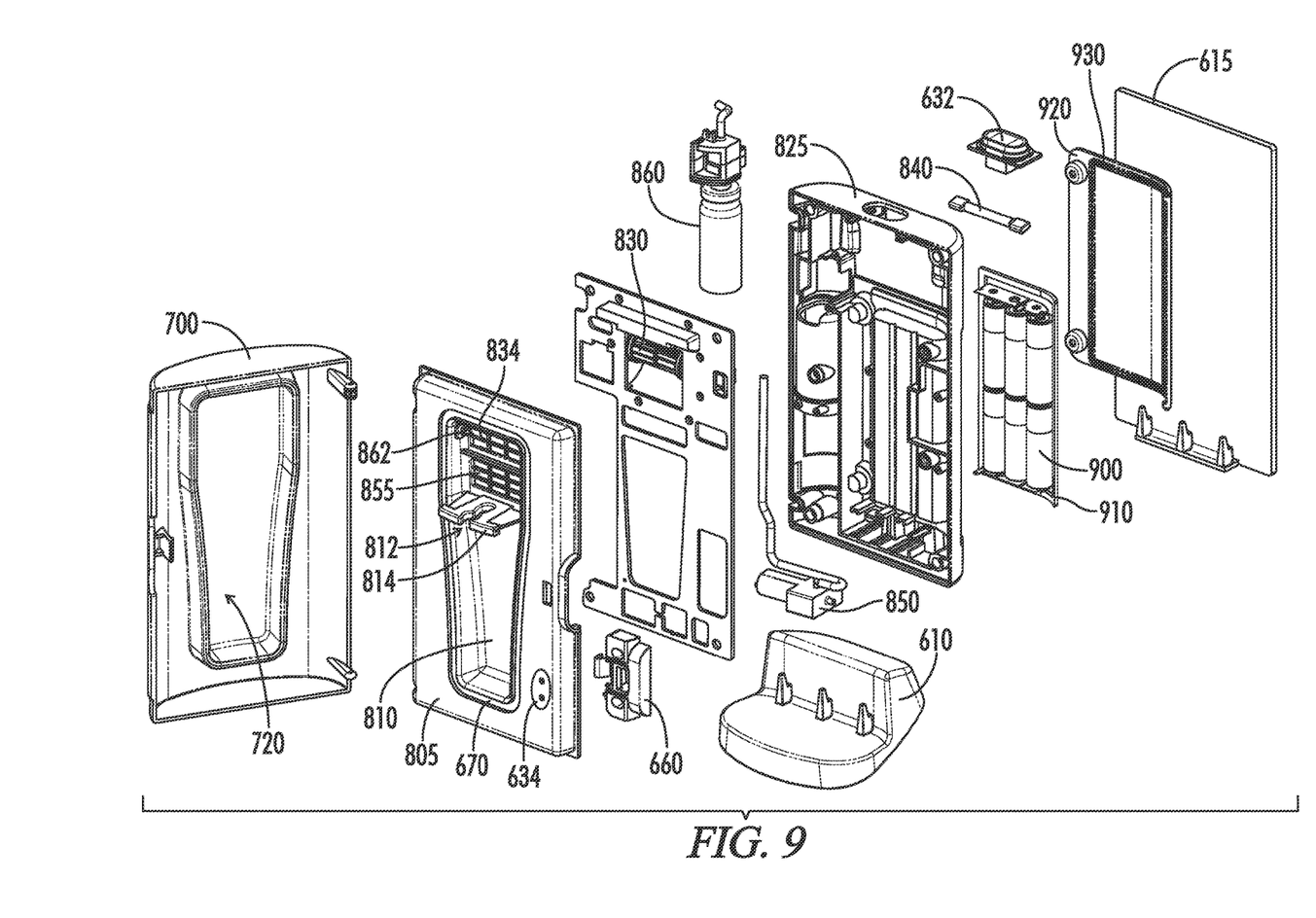
FIG. 9 is an exploded view of the device of FIG. 7.

FIG. 7 is a perspective view of an alternative embodiment of a dryer device 550 of the present invention in a closed position, with FIG. 8 illustrating the device 550 in the open position and FIG. 9 illustrating an exploded view of one embodiment of the assembly of the device 550. The embodiment of FIGS. 7-9 is similar in function to the embodiment of FIGS. 1-6 and therefore certain features of the embodiment of FIGS. 7-9 will not be described in detail.

One embodiment of the device 550 further comprises a housing 600 mountable on a base 610, a door 700 having a door cover 705, an exterior 710 and an interior 720 and that is movable relative to the housing 600 via a hinge 650 between a closed position as shown in FIG. 7 and an open position as shown in FIG. 8, and a latch 660 for securing the door 700 to the housing 600. In this particular embodiment, the base 610 is shaped to removably support the housing 600 in an upright position, although it will be understood that the housing 600 could also positioned in different orientations such as, for example, in a horizontal orientation, or the housing 600 could also engage with a mounting bracket 615 for securing the device 550 to a wall, for example, or it could be provided with suction cups (not shown) or other mounting components as desired.

The device 550 further comprises an interior 800 that is defined between the housing 600 and the door 700. The interior 800 is exposed when the door 700 is in the open position (FIG. 7), and is sealed from the ambient surroundings when the door 700 is in the closed position (FIG. 8). An air-tight seal for the interior 800 is created through the use an O-ring seal or gasket 670 defined between the housing 600 and the door 700, the seal 670 being embedded in or otherwise retained by either the housing 600 or the door 700. While an O-ring seal 670 is shown and described, it will be appreciated that other methods of sealing are contemplated.

The interior 800 further comprises a front housing 805 having a wall 810, a razor holder mount 820 provided in the wall 810, a rear housing 825 including dryer 830 with directional blades 834, a sanitizing light 840 such as an ultraviolet (UV) light, a vent 855 for the removal of air from the interior 800, a sanitizing spray 860 in communication with a nozzle 862 adjacent the vent 855 for delivery a spritz or a spray to a razor head (not shown) positioned adjacent the vent 855. The sanitizing spray 860 may deliver a mist of alcohol or other antiseptic through the nozzle 862. The dryer 830 could be provided with a heating element (not shown) if desired. A vacuum pump 850 disposed in the rear housing 825 is in fluid communication with the vent 855 in the interior 800 for purposes of evacuating the air from within the interior 800 when so desired and as described below. The powered components of the device 550 are controlled by a CPU (not shown, but see FIG. 6 for example) and energized by a power source 900 shown in the embodiment of FIG. 9 as a plurality of "AA" batteries that are retained in a chamber 910 in the rear housing 825 by a door 920 having an O-ring seal 930. While "AA" batteries are shown as the power source 900 in the embodiment of FIG. 9, it will be appreciated that other methods of powering the device 550 are contemplated as described above.

The razor blade holder 812 has gripping arms 814 that are dimensioned to receive the handle of a razor (now shown) or other instrument. The gripping arms 814 are flexible and resilient to allow for easy insertion and removal of a razor therefrom, and such arms 814 are spaced to accommodate most commonly dimensioned razor handles. In one embodiment, the razor blade holder 812 is fixedly attached to the wall 810. In an alternative embodiment, the razor blade holder 812 is removably attached to the wall 810 to allow for easy replacement or to allow for the attachment of interchangeable razor blade holders (not shown) of various dimensions for holding razors (not shown) of varying dimensions. In one embodiment, the device 550 could be provided with a variety of interchangeable holders (not shown) and the user would be required to select the holder that most comfortably fits whatever implement will be placed therein.

The razor blade holder 812 resides below the dryer 830 and the sanitizer light 840 so that the blade from a razor will be adjacent the dryer 830 and sanitizer 840 if the razor is positioned upright in the holder 812. While the vent 855 is shown in a certain location, it will be appreciated that it may be positioned anywhere within the interior 800 as long as it functions to remove air from within the interior 800 when desired. In one embodiment, the interior could be provided with multiple dryers and sanitizers (not shown) to account for the various positioning of the razor relative to the razor holder. In another embodiment, the dryer and sanitizer could reside on the door interior 720. Other arrangements are contemplated.

The housing 600 preferably comprises a switch 632 for activating the device 550 as will be described below and one or more indicators 634 for displaying a variety of operational parameters and functions including, but not limited to, power capacity of the power source 900 and the amount of sanitizing spray 860 remaining and whether the spray 860 should be replaced. This modular design of the housing 600 as shown in FIG. 9 allows for repair and easy access to the various components of the device 550.

One non-limiting embodiment of an operation of the device 550 of FIGS. 7-9 will now be described. A razor (not shown) is received within the gripping arms 814 of the razor holder 812 so that the blade of the razor faces the dryer 830. The door 700 is pivoted from the open position (FIG. 8) to the closed position (see FIG. 7) and the latch 660 is engaged to create an air-tight chamber in the interior 800 through the use of seal 670. Thereafter, a user (not shown) activates the switch 632 that causes a spritz of sanitizer spray 860 to be delivered to the razor blade(s) via outlet nozzle 862 and also activates a drying operation. In an alternative embodiment, the drying operation could be initiated simply by closing the door 700 and securing the door latch 660, although such embodiment may incorporate a sensor (not shown) into the razor holder 812 to ensure that the drying operation does not commence unless an implement is being retained by the holder 812. In yet another alternate embodiment, the engagement of the razor with the razor holder 812 could initiate the drying operation, whereby the vacuum 850 would not be activated unless the door 700 is closed and the interior 800 is sealed. Other activation methods are contemplated.

The drying operation can be carried out in a number of ways. In a preferred embodiment, activation of the switch 632 energizes the dryer 830 in accordance with a timer that that is controlled by a central processing unit (CPU) control system such as a processor or printed circuit board (PCB) provided in the housing 600. In a preferred embodiment, the drying of the blade is accomplished by a flow of air created by the fan 830 for a certain period of time such as, but not limited to, approximately three minutes, which flow of air is drawn across the blade and evacuated through the vent 855 into the environment outside of the device 550. Based on a number of environmental factors, such as the relative humidity and temperature of the surroundings, the fan operation may range, for example, from about two minutes to about ten minutes. Other drying times are contemplated. In other embodiments, a heater element (not shown) such as a resistive heating element is incorporated into the fan airstream to heat and dehumidify the blown air or otherwise accelerate the drying operation and reduce the drying time. In an alternative embodiment, the drying operation may be controlled by a humidity sensor (not shown) that evaluates the relative humidity in the interior 800 and terminates the drying operation once a certain humidity level is reached.

In a preferred embodiment, the sanitizer light 840, such as an ultraviolet (UV) light, is also activated during the drying operation. In an alternative embodiment, the sanitizer light is activated after the drying operation is complete. The sanitizing spray 860 may also be applied manually by the user or automatically as part of the operation of the device 550 during the drying and sanitizing operation for example. For example, activation of the switch 632 while the door 700 is open and a razor is engaged in the holder 812 may cause the delivery of a spritz of sanitizing spray 860 without an accompanying heating operation. The purpose of any cleaning solution is to remove any oils or salts that remain on the blades after being used and to lubricate the blades, while the sanitizer light is used to kill any bacteria remaining on the blades.

The drying operation is preferably controlled by a timer or a humidity sensor or both. Depending upon the amount of air flow and heat generated, if any, the time for the drying operation can be determined experimentally to provide a suitable level of drying of the razor blade. During or after the drying operation, the vacuum pump 850 evacuates air and moisture through the vent 855 and out of the interior 800 and seals the interior 800 in order to maintain a dry and suitable environment for the stored razor and to prevent oxidation at the blades until it is desired to use the razor again. If a humidity sensor is employed, the drying operation may automatically repeat without user intervention if the relative humidity within the vacuum-sealed interior 800 reaches a certain level. A valve (not shown) is provided to maintain a vacuum seal within the interior 800 once a sufficient amount of air has been evacuated. In one embodiment, pressing of the switch 632 with a vacuum in the interior 800 acts to release the vacuum and enable the user to open the door 700. In another embodiment, a separate button (not shown) could be used to release the vacuum seal, or it can occur simply by disengaging the latch 660.

A display (not shown) may be incorporated in the housing 600 and various parameters may be indicated on such display, such as the time of day, the ambient temperature, whether an implement is being retained by the holder 812, the time duration of the drying operation, the amount of time left in the drying operation, whether the sanitizer light 840 is activated, whether the sanitizer spray 860 is almost empty, whether the vacuum 850 is activated, the relative humidity within the interior 800, whether the interior 800 is vacuum sealed, and whether the device 550 is either turned off or not active. The display may also show whether the device 550 is connected to an external power source such as home current, or whether the device 550 is running on battery power 900 and the amount of battery life remaining. Other operational parameters are contemplated.

Figure 10:
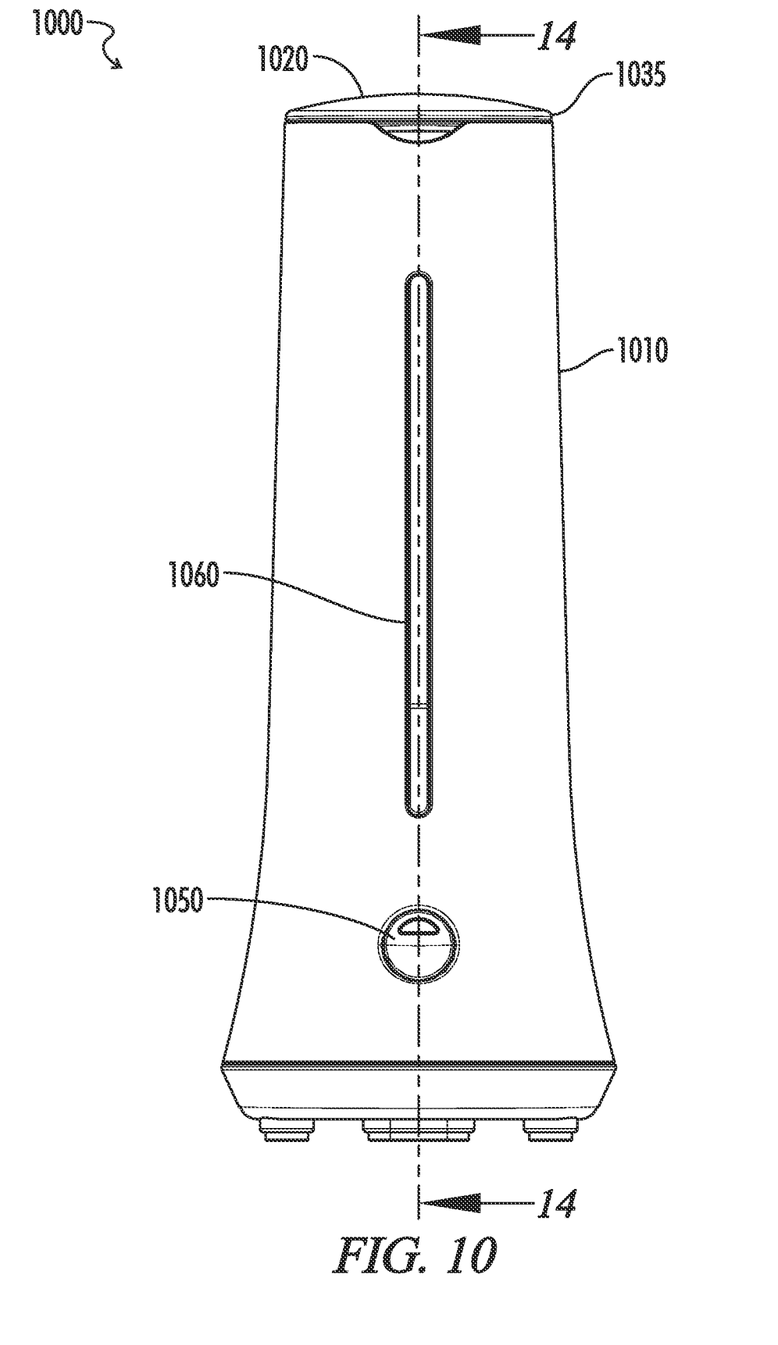
FIG. 10 is a front view of another embodiment of a hygienic razor blade dryer device of the present invention in the closed position.
Figure 11:
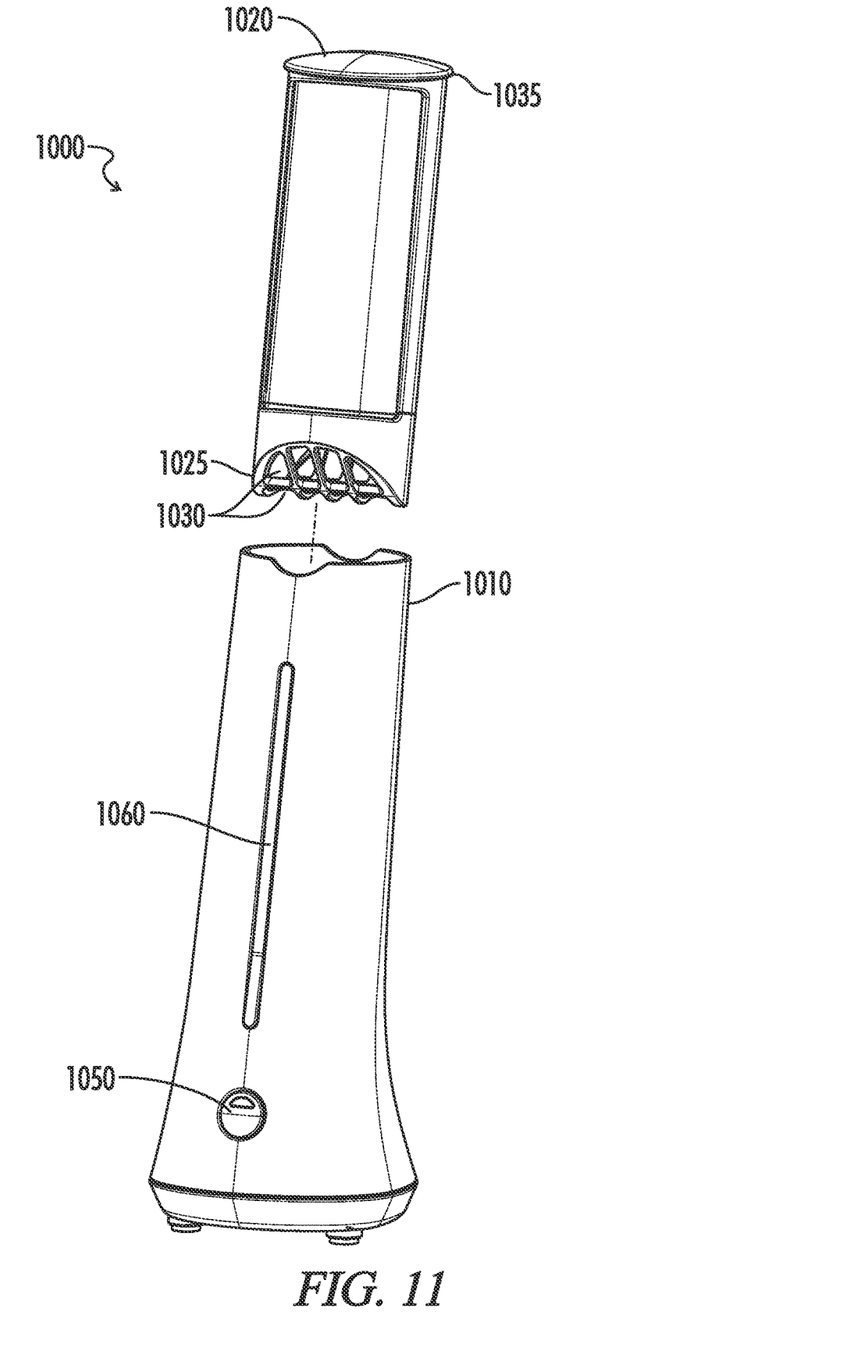
FIG. 11 is a perspective view of the hygienic razor blade dryer of FIG. 10 in an open position.
Figure 12:
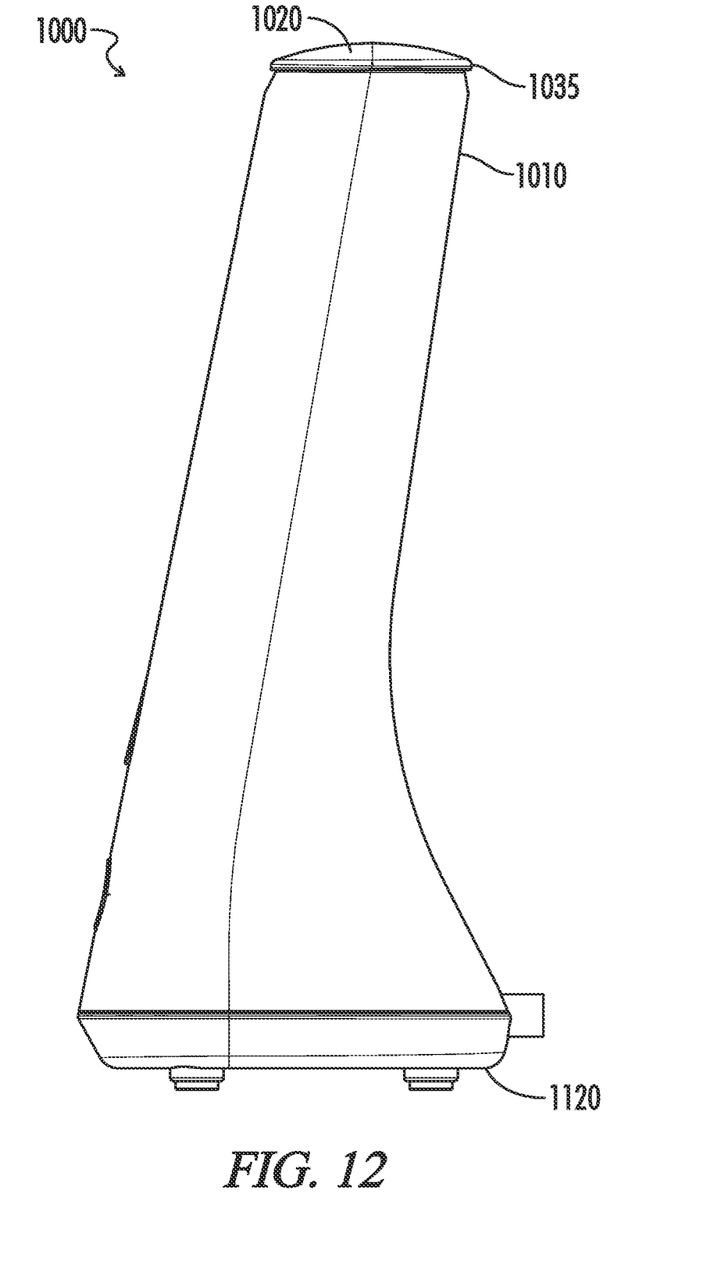
FIG. 12 is a side view of the hygienic razor blade dryer device of FIG. 10 in the closed position.
Figure 13:
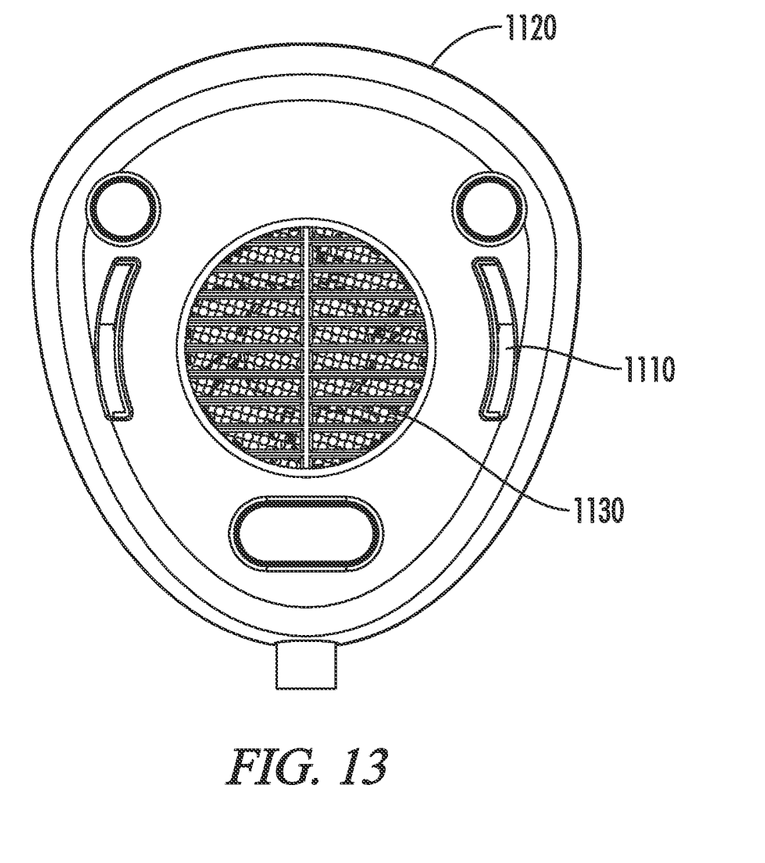
FIG. 13 is a bottom view of the hygienic razor blade dryer device of FIG. 10.
Figure 14:
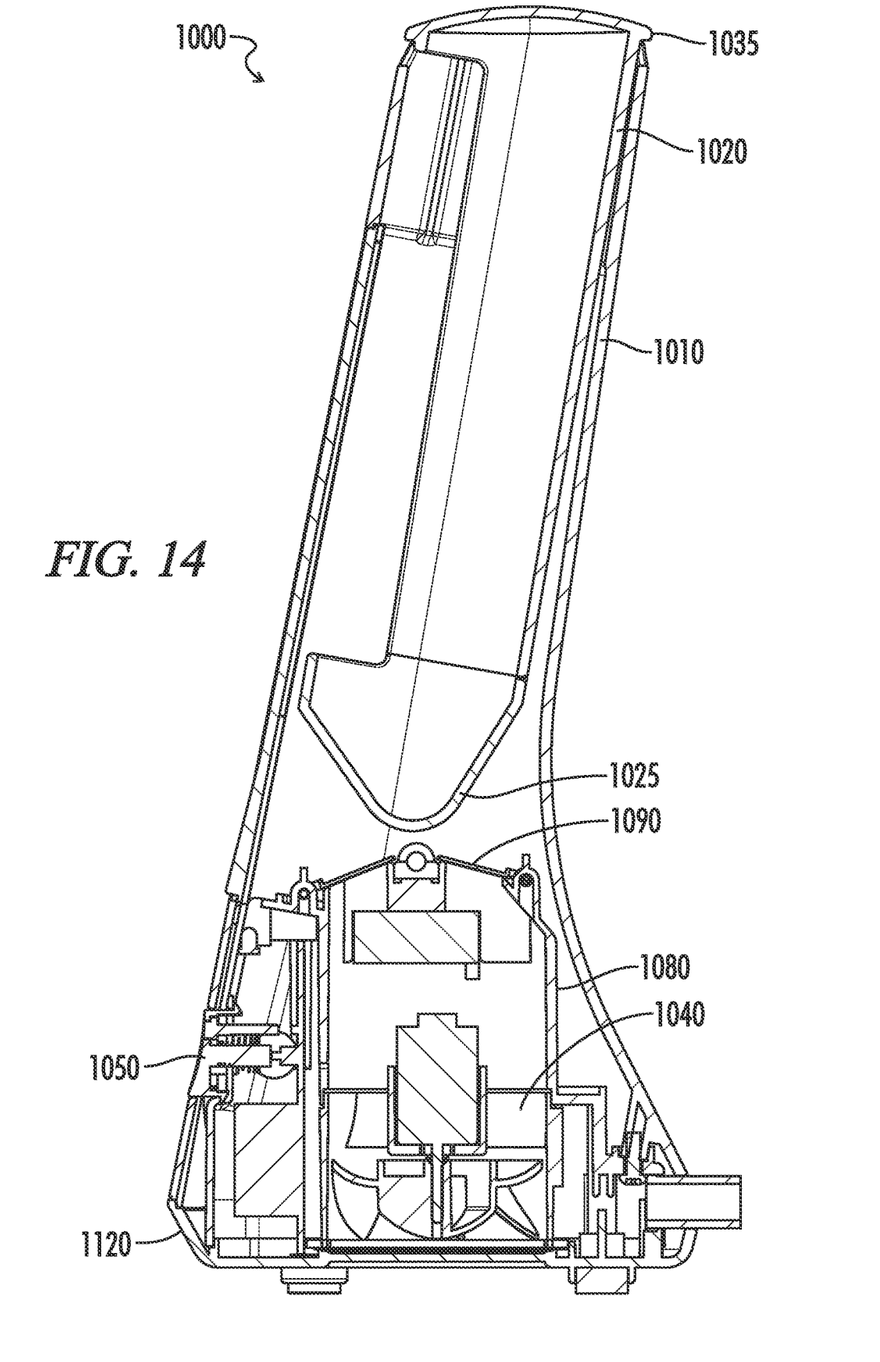
FIG. 14 is a sectioned view of the hygienic razor blade dryer device of FIG. 10 taken along line 14-14 of FIG. 10.
Figure 15:
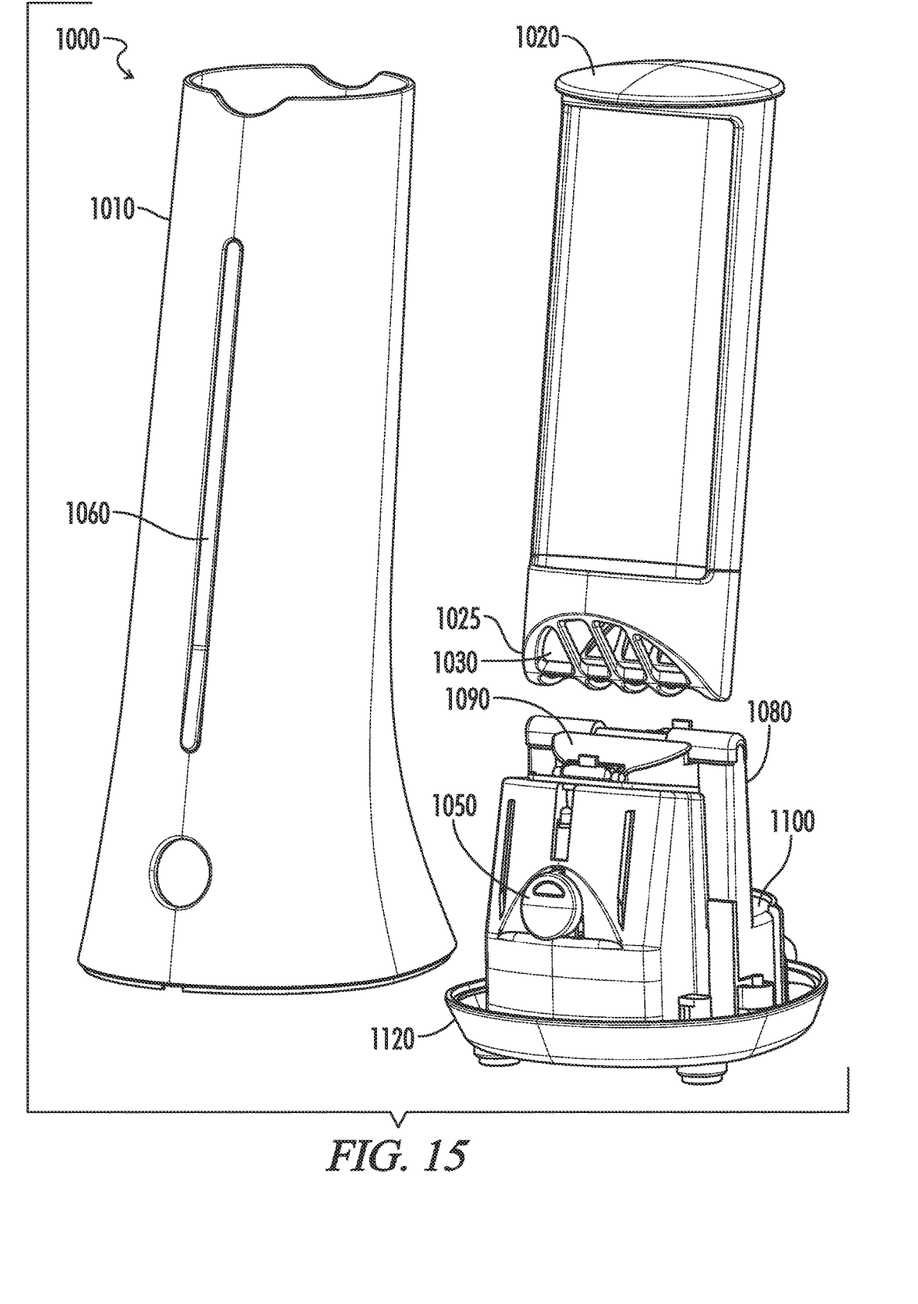
FIG. 15 is a partially exploded view of the hygienic razor blade dryer device of FIG. 10.
Figure 16:
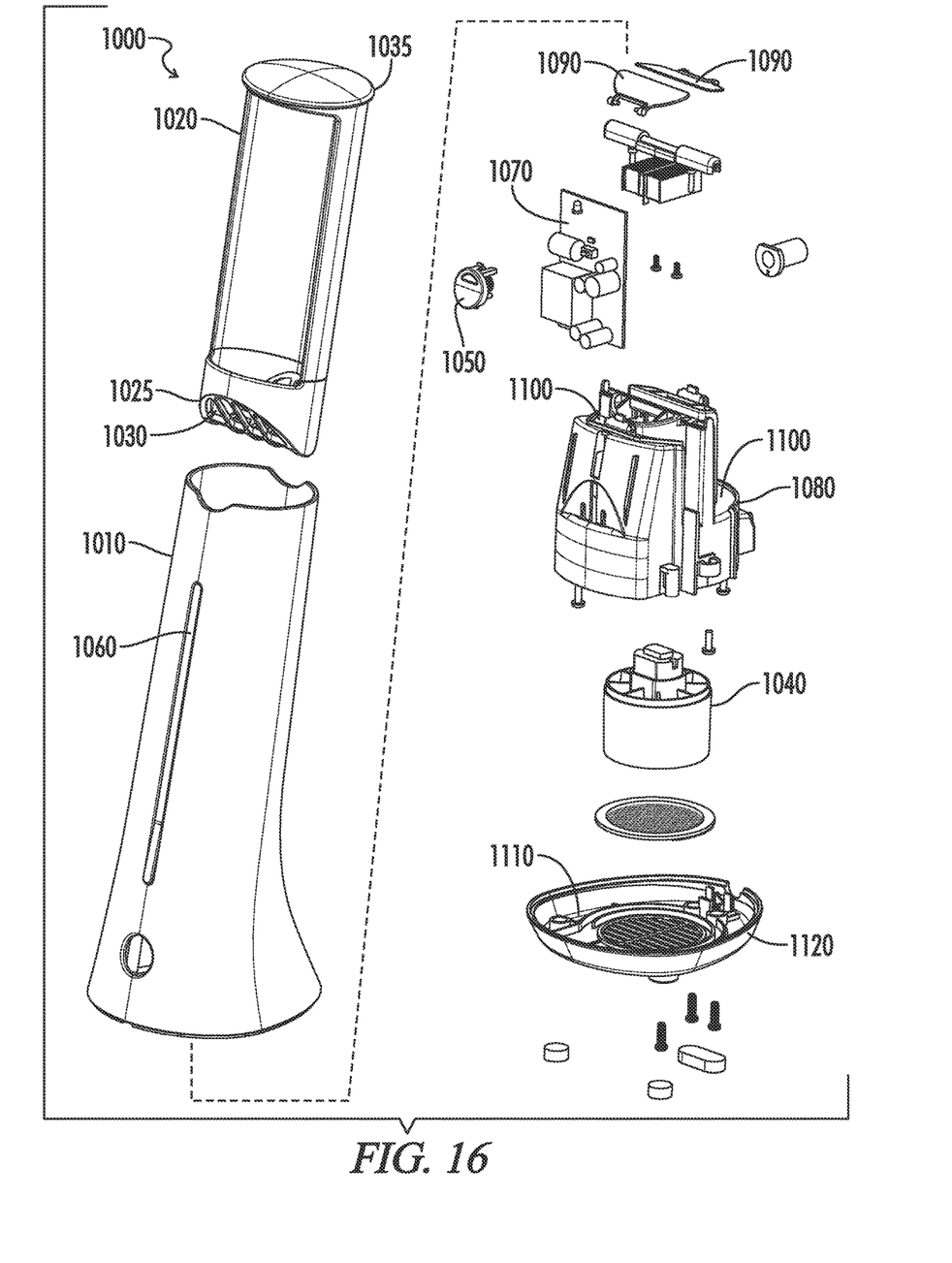
FIG. 16 is an exploded view of the hygienic razor blade dryer device of FIG. 10.

FIG. 10 is a front view of another embodiment of a hygienic razor blade dryer device 1000 of the present invention in the closed position, with FIG. 11 illustrating the device in an open position, FIG. 12 showing a side view, and FIG. 13 showing a bottom view. FIG. 14 shows a sectioned view of the hygienic razor blade dryer device of FIG. 10 taken along line 14-14 of FIG. 10. FIG. 15 is a partially exploded view of the device 1000 and FIG. 16 is a fully exploded view.

The device 1000 has an outer housing 1010 and a carriage 1020 adapted to receive a razor having a razor blade (not shown). The outer housing 1010 is adapted to receive the carriage 1020, and the carriage may then slide into the outer housing 1010. A first end 1025 of the carriage 1020 forms a basket having at least one aperture 1030 such that water can drain out of the carriage and air can pass into and out of the carriage 1020 from the outer housing 1010. The aperture 1030 may be a combination of multiple apertures, or a grid design, or any other configuration so long as air may pass through the aperture 1030 and into the carriage 1020 and the basket can support the razor. Typically, when a razor is placed in the carriage, the head of the razor, containing the razor blade, is placed in the basket at the first end 1025 of the carriage 1020 such that the handle of the razor sticks upwards.

The carriage 1020 has an upper lip 1035, such that when the outer housing 1010 receives the carriage, the carriage, and its contents, are suspended within the outer housing 1010 by the upper lip. When suspended within the housing, the end 1025 of the carriage 1020 forming a basket supports the contents of the carriage, typically a razor having a razor blade. Although the device 1000 is described as being used to dry a razor blade in a razor, it could be used to dry any number of other devices.

The outer housing further contains a dryer 1040, such as a fan. In some embodiments, the dryer 1040 may further comprise, or may be used in combination with, a heating element. The outer housing 1010 further contains a button 1050 for activating the device once the carriage 1020 is placed within the outer housing 1010. When the carriage 1020 is placed within the outer housing 1010, the first end 1025 of the carriage 1020, with the aperture 1030, is in drying communication with the drying element 1040, such that the drying element can effectively dry a razor blade held in the head of a razor placed within the basket at the first end 1025 of the carriage 1020.

The outer housing 1010 may further comprise a window 1060, which may indicate to a user whether a razor is present within the carriage 1020. In some embodiments, a light may replace the window 1060, and the light may be activated to indicate when the device 1000 is activated. Alternatively, a light may be provided within the outer housing 1010 such that the window 1060 lights up when the light is on.

The outer housing 1010 of the device 1000 may further be provided with electronics 1070 for controlling a drying sequence for the device. The outer housing 1010 may further contain sensors, such as humidity sensors, which may provide data to the electronics 1070 in order to better control a drying sequence of the device.

Within the outer housing 1010, an inner housing 1080 may be provided for arranging and protecting components of the device 1000. The inner housing 1080 may protect other components, such as the electronics 1070 and the fan 1040 by isolating such components from any water within the outer housing 1010. The inner housing 1080 may further comprise additional parts for protecting internal components from water while allowing the functionality of the dryer 1040, such as flaps 1090 which deflect water towards drainage tracks 1100. The drainage tracks 1100 may direct water towards a drainage outlet 1110 in a base 1120 of the device 1000. The base 1120 further contains venting 1130 for increasing the effectiveness of the dryer 1040

When in use, a razor having a razor blade is placed into carriage 1020, which is then placed into outer housing 1010. When placing the razor within the carriage 1020, a head of the razor containing a razor blade is positioned in the basket at the first end 1025 of the carriage 1020. The carriage 1020 is then moved to a closed position, so that the razor blade, in the first end 1025 of the carriage 1020 is positioned in drying communication with the dryer. Water still on the razor blade may drip through the apertures 1030, and may then be deflected by the flaps 1090 towards the drainage tracks 1100 and out of the system through drainage outlet 1110 in the base. The dryer 1040 may then be activated, blowing the flaps 1090 out of the way and blowing air through the apertures 1030 and across the razor blade, drying it.

In some embodiments, the dryer 1040 may work in concert with a vacuum pump and the lip 1035 of the carriage 1020 may form a seal with the outer housing 1010. In other embodiments, a control panel may be incorporated for more sophisticated operating sequences than those operated by the button 1050.

The device of the present invention can be constructed in several different price points. For example, a baseline economy version may not include a sanitizer light, vacuum pump or a display and may simply include a dryer that activates with the push of a single switch for a predetermined period of time. The next level up may include a sanitizer spray and sanitizer light that is activated along with the dryer. The next level up may include a humidity sensor that automatically triggers the dryer when the relative humidity reaches a certain level in the interior, and a display for monitoring the same. The next level up may include a vacuum pump in combination with a dryer and a sanitizer light and spray.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention. Furthermore, the foregoing describes the invention in terms of embodiments foreseen by the inventor for which an enabling description was available, notwithstanding that insubstantial modifications of the invention, not presently foreseen, may nonetheless represent equivalents thereto.

What is claimed is:

1. A hygienic razor blade dryer comprising:
   a) an outer housing having a housing interior;
   b) a carriage having a carriage interior adapted to receive a razor having a razor blade, wherein the outer housing is adapted to removably receive the carriage; and
   c) a dryer for drying a razor blade disposed within the carriage interior,
   d) wherein an end of the carriage has at least one aperture such that, when received by the outer housing, the carriage interior is in drying communication with the dryer.

2. The hygienic razor blade dryer of claim 1, wherein the carriage is movable between an open position at least partially removed from the housing interior for access to the razor and a closed position for placing the carriage interior in drying communication with the dryer.

3. The hygienic razor blade dryer of claim 1, further comprising a window for determining if a razor is present within the carriage.

4. The hygienic razor blade dryer of claim 1, further comprising flaps between the carriage and the dryer for deflecting fluid dripping from the razor towards a drainage outlet.

5. The hygienic razor blade dryer of claim 1, further comprising a button for activating the dryer.

6. A hygienic razor blade dryer comprising:
   a) an outer housing having a housing interior and a carriage having a carriage interior that is movable between an open position at least partially removed from the housing interior for access to the carriage interior and a closed position for placing the carriage within the housing interior, the carriage adapted to receive a razor containing a razor blade;
   b) a dryer for drying the razor blade; and
   c) an inner housing within the outer housing for protecting internal components from fluid within the outer housing,
   wherein the dryer is within the inner housing.

7. The hygienic razor blade dryer of claim 6 wherein an end of the carriage has an aperture, such that the carriage interior is in drying communication with the dryer in the closed position.

8. The hygienic razor blade dryer of claim 6, the inner housing further comprising a flap for deflecting fluid dripping from the razor, the flap disposed between the carriage and the dryer.

9. The hygienic razor blade dryer of claim 8, the inner housing further comprising a drainage track for routing fluid to a drainage outlet.

10. A method of drying a razor blade comprising:
    a) providing a drying device having an interior, a carriage that is movable between an open position for access to the carriage and a closed position for placing the carriage within the interior, and a dryer;
    b) inserting a razor having a razor blade into the carriage and moving the carriage to the closed position; and
    c) activating the dryer for a period of time to dry the razor blade,
    wherein an end of the carriage has at least one aperture such that an interior of the carriage is in drying communication with the dryer when the carriage is in the closed position.

11. The method of claim 10, wherein the drying device further comprises an inner housing within the interior of the drying device, the inner housing containing the dryer.

12. The method of claim 11, wherein the inner housing further comprises a flap for deflecting fluid dripping from the razor, the flap disposed between the carriage and the dryer.

13. The method of claim 10, further comprising a processor for controlling the dryer activation.

* * * * *